(12) United States Patent
Tasso et al.

(10) Patent No.: US 7,968,610 B2
(45) Date of Patent: Jun. 28, 2011

(54) PROCESS FOR STABILIZING THE PERFORMANCES OF A CATALYST FOR FISCHER TROPSCH REACTION

(75) Inventors: Andrea Tasso, Zelo Buon Persico (IT); Stefano Rossini, Milan (IT); Paolo Pollesel, San Donato Milanese (IT)

(73) Assignees: ENI S.p.A., Rome (IT); Institut Francais du Petrole, Rueil Malmaison (FR)

( * ) Notice: Subject to any disclaimer, the term of this patent is extended or adjusted under 35 U.S.C. 154(b) by 0 days.

(21) Appl. No.: 12/811,383

(22) PCT Filed: Dec. 29, 2008

(86) PCT No.: PCT/EP2008/011174
§ 371 (c)(1),
(2), (4) Date: Oct. 4, 2010

(87) PCT Pub. No.: WO2009/086924
PCT Pub. Date: Jul. 16, 2009

(65) Prior Publication Data
US 2011/0039953 A1 Feb. 17, 2011

(30) Foreign Application Priority Data

Jan. 4, 2008 (IT) .............................. MI2008A0007

(51) Int. Cl.
*C07C 27/00* (2006.01)
(52) U.S. Cl. ....................................... 518/700; 518/728
(58) Field of Classification Search .................. 518/700, 518/728
See application file for complete search history.

(56) References Cited

U.S. PATENT DOCUMENTS

2011/0009502 A1* 1/2011 Marion et al. ................ 518/715

OTHER PUBLICATIONS

Krishnamoorthy, Sundaram et al., "An Investigation of the Effects of Water on Rate and Selectivity for the Fischer-Tropsch Synthesis on Cobalt-Based Catalysts", Journal of Catalysis, vol. 211, No. 2, pp. 422-433, XP002578680, (Oct. 25, 2002).
Bertole, J. Christopher et al., "The Effect of Water on the Cobalt-Catalyzed Fischer-Tropsch Synthesis", Journal of Catalysis, vol. 210, No. 1, pp. 84-96, XP002578681, (Aug. 15, 2002).
Tavasoli, A. et al., "Raising Co/Al$_2$O$_3$ catalyst lifetime in Fischer-Tropsch synthesis by using a novel dual-bed reactor", Fuel Processing Technology, vol. 88, No. 5, pp. 461-469, XP002578682, (May 2007).
Dalai, A.K. et al., "Review Fischer-Tropsch synthesis: A review of water effects on the performances of unsupported and supported Co catalysts", Applied Catalysis A: General , vol. 348, No. 1, pp. 1-15, XP002578683, (Sep. 30, 2008).
Schanke, D. et al., "Study of the deactivation mechanism of Al$_2$O$_3$-supported cobalt Fischer-Tropsch catalysts", Catalysis Letters, vol. 34, No. 3-4, pp. 269-284, XP002578684, (Sep. 1995).
Hilmen, A.M. et al., "Study of the effect of water on alumina supported cobalt Fischer-Tropsch catalysts", Applied Catalysis A: General, vol. 186, No. 1-2, pp. 169-188, XP002578685, (Oct. 4, 1999).
Claeys, Michael et al., "On the effect of water during Fischer-Tropsch synthesis with a ruthenium catalyst", Catalysis Today, vol. 71, No. 3-4, pp. 419-427, XP002580229, (Jan. 15, 2002).
Zhang, Yulong et al., "Effect of Water Vapor on the Reduction of Ru-Promoted Co/Al$_2$O$_3$", Journal of Catalysis, vol. 188, No. 2, pp. 281-290, XP002578686, (Dec. 10, 1999).
Li, Jinlin et al., "Fischer-Tropsch synthesis: effect of water on the deactivation of Pt promoted Co/Al$_2$O$_3$ catalysts", Applied Catalysis A: General, vol. 228, No. 1-2, pp. 203-212, XP002578687, (Apr. 30, 2002).
Van Berge, P.J. et al., "Oxidation of cobalt based Fischer-Tropsch catalysts as a deactivation mechanism", Catalysis Today, vol. 58, No. 4, pp. 321-334, XP002578688, (May 26, 2000).

* cited by examiner

*Primary Examiner* — Jafar Parsa
(74) *Attorney, Agent, or Firm* — Oblon, Spivak, McClelland, Maier & Neustadt, L.L.P.

(57) ABSTRACT

Process for maintaining the stability of performances of a catalyst for Fischer-Tropsch reaction, performed in a slurry bubble column reactor under a triphase system which comprises gradually increasing the $P_{H2O}/P_{H2}$ ratio and the $P_{H2O}/Z$ ratio, during the start-up phase, with $Z = _{P0} \cdot (T/T_1)^4 \cdot e^{-(K2/(t \cdot K3))}$ from 0.4 to 0.8, for a period of time not shorter than 100-150 hrs and not longer than 200-300 hours and, at the end of the start-up phase, maintaining the $P_{H2O}/P_{H2}$ and $P_{H2O}/Z$ ratios substantially equal to or lower than 0.8.

1 Claim, No Drawings

PROCESS FOR STABILIZING THE PERFORMANCES OF A CATALYST FOR FISCHER TROPSCH REACTION

The present invention relates to a process for stabilizing the performances of a catalyst for Fischer-Tropsch reaction.

More specifically, the present invention relates to a process for controlling the initial phases of Fischer-Tropsch reaction with synthesis gas so as to stabilize the performances of the cobalt-based catalyst supported on stabilized alumina, operating in fluid bed or slurry bubble column reactors.

As is known, the conversion of synthesis gas (mixture including hydrogen, carbon monoxide and possibly carbon dioxide) into hydrocarbons, has been developed since the beginning of the twentieth century and is conventionally defined as Fischer-Tropsch synthesis. Production plants constructed in Germany and South Africa, some of them still in operation, essentially dedicated to the production of synthetic fuels, operate with iron-based catalysts.

More recently, a new interest towards this type of synthesis has led to the development of catalysts based on cobalt, particularly active, when the Fischer-Tropsch reaction is carried out in slurry bubble column reactors, to produce heavier hydrocarbons, essentially $C_{5+}$ paraffins, i.e. paraffin hydrocarbons with at least five carbon atoms in the molecule, reducing the formation of methane and $C_2$-$C_4$ hydrocarbons to the minimum. The hydrocarbon thus obtained can then be transformed, in a hydrocracking unit downstream, into lighter products which fall within the definitions of kerosene-type fuels or "diesel fuel". A process of this type is described in European patent 1,406,988.

The use of cobalt-based catalysts is more convenient when the Fischer-Tropsch reaction is carried out with synthesis gases rich in hydrogen, which are obtained, as is known, from the oxidation of methane.

Numerous formulations based on cobalt have been described in literature as catalysts for the Fischer-Tropsch synthesis. See, for example, European patent EP 313,375 and 1,233,011. Contrary to iron-based catalysts, which are active towards the conversion reaction of CO with $H_2O$ (according to the so-called "water gas shift reaction" $CO+H_2O=CO_2+H_2$), cobalt-based catalysts show a very poor activity towards this reaction (B. H. Davis, Catalysis Today, 84, 2003, page 83). Consequently, also as a result of the reaction conditions used, for example pressure and temperature, during the Fischer-Tropsch reaction carried out in the presence of cobalt-based catalysts, a high partial water vapour pressure can be generated which negatively influences the catalyst activity, causing its rapid degradation.

The negative effect of water on the Fischer-Tropsch cobalt catalyst is described in M. Rothaemel, Catalysis Today, Vol. 38, Issue 1, 1997, 79-84, which specifies the deactivation of the cobalt catalyst supported on alumina due to the oxidative effect of the water towards the surface metal cobalt, and in P. J. van Berge, Catalysis Today, Vol. 58, Issue 4, May 2000, 321-334, which points out that the oxidation phenomenon of cobalt is linked to the $P_{H2}/P_{H2O}$ ratio between the partial pressure of hydrogen and water.

It is also known, however, that the water produced during Fischer-Tropsch reaction has also the effect of increasing the catalytic activity, as explained in J. Catal. 211, 2002, 422, and also has a positive effect on the selectivity of the reaction. Consequently, in order to have good management of the Fischer-Tropsch reaction, it is advisable to have a good control of the $P_{H2O}/P_{H2}$ ratio inside the synthesis reactor.

In particular, it has been found that by adopting particular operative conditions described hereunder, mainly during the start-up phase of the reaction, when this is performed in triphase reactors (known as slurry reactors) wherein a gas phase (synthesis gas) is gurgled through a liquid phase (hydrocarbons) in which a solid phase is dispersed as fine particles (catalyst), it is possible to maintain the activity of the catalyst substantially stable, also during the subsequent normal running of the reactor.

An object of the present invention therefore relates to a process for maintaining the stability of the performances of a catalyst for Fischer-Tropsch reaction carried out in a slurry bubble column reactor, in which a solid phase, consisting of a metal cobalt-based catalyst in finely subdivided form, is dispersed in a continuous liquid phase consisting of hydrocarbons, and is kept in suspension by a gaseous phase consisting of synthesis gas, which passes through said liquid phase, in the form of bubbles, comprising:

(1) in the reaction start-up phase, regulating the operative variables, among which, prevalently, the flow-rate of the synthesis gas (but also, for example, the total pressure and temperature inside the reactor and the composition of the synthesis gas), so that the $P_{H2O}/P_{H2}$ ratio between the partial water pressure ($P_{H2O}$) generated during the reaction, and the partial hydrogen pressure ($P_{H2}$) gradually increases from 0.4 to 0.8 (without substantially exceeding these limits) for a period of time not shorter than 100-150 hrs and not longer than 200-300 hrs;

(2) in the reaction start-up phase, regulating the operative variables, among which, prevalently, the flow-rate of the synthesis gas (but also, for example, the total pressure and temperature inside the reactor and the composition of the synthesis gas), so that the $P_{H2O}/Z$ ratio gradually increases from 0.4 to 0.8 (without substantially exceeding these limits) for a period of time not shorter than 100-150 hrs and not longer than 200-300 hrs, wherein Z is given by the following equation:

$$Z = P_0 \cdot (T/T_1)^4 \cdot e^{-(K2/(t \cdot K3))}$$

wherein
$P_0$=1 bar
$T_1$=100° C.
T=temperature inside the reactor, in ° C.
K2=constant equal to 7745 K·nm
t=temperature inside the reactor as K
K3=average diameter of the catalyst pores; and c. at the end of the start up, maintaining the $P_{H2O}/P_{H2}$ and $P_{H2O}/Z$ ratios substantially the same as, or lower than 0.8, by operating on the same operative parameters of the two phases previously described.

According to the present invention, the term "start-up phase" as used in the present description and in the claims, means the initial operative phase of the synthesis reaction, which includes a first phase of catalyst loading and a second phase of catalyst conditioning.

The first phase for loading the catalyst comprises:
a) incorporating the catalyst, previously reduced, in a matrix of paraffin waxes, for example in the form of cylinders, pellets or granules, solid at room temperature. The quantity of wax in the matrix ranges from 30 to 70% by weight;
b) melting, in a container (A) maintained at a high temperature, the paraffin matrix together with a diluent, for example a single oligomers of $C_6$-$C_{18+}$ α-olefins or any mixture of them, which is miscible with the molten paraffin matrix and which is in the form of a liquid both under the conditions present in the container and at room temperature. A flow of inert gas is distributed from the bottom of said container (A), for example nitrogen or purified natural gas (methane), in order to obtain a sufficiently homogeneous suspension. The catalyst englobed in the paraffin matrix is heated to a temperature equal to or higher than 150° C., for example from 150 to 220° C. and diluted until a solid concentration ranging from 10 to 50% by weight is obtained;

c) pressurizing the container (A) in which the complete melting of the paraffin matrix has taken place at a pressure higher than that of the reactor (B), maintaining the system fluidized by the continuous introduction of inert gas from the bottom of said container (A). The pressure in the container (A) is normally higher than that of the container (B) by about 0.1-0.4 MPa, whereas the pressure inside the reactor is maintained at 0.1-1 MPa;

d) transferring, by means of the pressure jump, the diluted solution from container (A) under pressure to the reactor (B), initially empty, maintained at a temperature higher than or equal to that present in the container (A) and also flushed with inert gas from the bottom. A flow of inert gas is maintained at the bottom of reactor (B) during the whole transfer procedure to guarantee the suspension of the catalyst preventing its sedimentation;

e) repeating steps (b) to (d) until the normal operative level of suspension is reached in the reactor (B) and in the possible external equipment envisaged for the treatment of the suspension (for example degasifier, liquid-solid separators, pumps, etc.).

At the end of the loading phase, the second conditioning phase of the catalyst is performed, before bringing the system to the normal reaction and production conditions. More specifically, once the loading has been completed, the reactor is under temperature conditions ranging from 150 to 220° C. with a pressure of 0.1 to 1 MPa, and is continuously fed with inert gas. The conditioning phase of the reactor includes:

a) regulating the temperature and pressure to the values envisaged for the conditioning, i.e. ranging from 200 to 230° C. and from 0.5 to 1.5 MPa;

b) gradually substituting the inert gas with synthesis gas until the concentration of inert gas ranges from 5 to 50% by volume and maintaining a partial water pressure (co-product of the Fischer-Tropsch synthesis reaction) lower than 1.0 MPa, preferably lower than 0.5 MPa, more preferably lower than 0.3 MPa, in order to satisfy the above constraints as per (1) and (2);

c) maintaining the conditions of point (b) for a period of 24-72 hours;

d) gradually increasing the pressure inside the reactor to regime values (0.5-5 MPa), continuing to satisfy the relations (1) and (2);

e) gradually reducing the concentration of inert gas to optimal minimum level until regime conditions are reached, continually satisfying the constraints as per (1) and (2); and subsequently f) gradually increasing the reaction temperature until regime values are reached (200-350° C.) continually satisfying the constraints as per (1) and (2) and, after a time ranging from 100-150 to 200-300 hrs the relation (3).

The synthesis gas essentially consists of CO and $H_2$, possibly in a blend with $CH_4$, $CO_2$ and inert gas in general, it has a $H_2$/CO molar ratio ranging from 1 to 3 and preferably comes from steam reforming and/or from the partial oxidation of natural gas or other hydrocarbons, on the basis of the reactions described, for example, in U.S. Pat. No. 5,645,613. Alternatively, the synthesis gas can come from other production techniques, such as, for example, autothermal reforming, C.P.O. (Catalytic Partial Oxidation) or from the gasification of coal with water vapour at high temperature, as described in Catalysis Science and Technology", vol. 1, Springer-Verlag, New York, 1981.

Even if any catalyst which is active in Fischer-Tropsch reaction could be used in the process, object of the present invention, the preferred catalyst according to the present invention is Co-based, dispersed on a solid carrier consisting of at least one oxide selected from one or more of the following elements: Si, Ti, Al, Zr, Mg. Preferred carriers are silica, alumina, titania or blends thereof.

The metal cobalt is present in the catalyst in quantities of 1 to 50% by weight, generally from 5 to 35% with respect to the total weight.

The catalyst used in the process object of the present invention can include further additional elements. For example it can include, with respect to the total, from 0.05 to 5% by weight, preferably from 0.1 to 3% of ruthenium and from 0.05 to 5% by weight, preferably from 0.1 to 3% of at least a third element selected from those belonging to group 3 (IUPAC regulation). Catalysts of this type are known in literature and described together with their preparation, in European patent 756,895.

Further examples of catalyst are still cobalt-based but containing tantalum, as promoter, in a quantity of 0.05-5% by weight, with respect to the total, preferably 0.1-3%.

These catalysts are prepared by first depositing a cobalt salt on the inert carrier (silica or alumina), for example by means of the dry impregnation technique, followed by a calcination step and, optionally, a reduction and passivation step of the calcined product.

A derivative of tantalum (particularly tantalum alcoholates) is deposited on the catalytic precursor thus obtained, preferably by means of the wet impregnation technique followed by calcination and, optionally, reduction and passivation.

The catalyst, whatever its chemical composition may be, is used in the form of finely subdivided powder with an average diameter of the granules ranging from 10 to 250 μm and an average pore diameter ranging from 0.1 to 100 nm, preferably from 1 to 50 nm.

The invention claimed is:

1. A process for maintaining the stability of the performances of a catalyst for Fischer-Tropsch reaction carried out in a slurry bubble column reactor, wherein a solid phase, consisting of a metal cobalt-based catalyst in finely subdivided form, is dispersed in a continuous liquid phase consisting of hydrocarbons, and is kept in suspension by a gaseous phase consisting of synthesis gas, which passes through said liquid phase, in the form of bubbles, comprising:
  a. in the reaction start-up phase, regulating the operative variables, among which, prevalently, the flow-rate of the synthesis gas, so that the $P_{H2O}/P_{H2}$ ratio between the partial water pressure ($P_{H2O}$) generated during the reaction, and the partial hydrogen pressure ($P_{H2}$) gradually increases from 0.4 to 0.8 (without substantially exceeding these limits) for a period of time not shorter than 100-150 hrs and not longer than 200-300 hrs;
  b. in the reaction start-up phase, regulating the operative variables, among which, prevalently, the flow-rate of the synthesis gas, so that the $P_{H2O}/Z$ ratio gradually increases from 0.4 to 0.8 (without substantially exceeding these limits) for a period of time not shorter than 100-150 hrs and not longer than 200-300 hrs, wherein Z is given by the following equation:

$$Z = P_0 \cdot (T/T_1)^4 \cdot e^{-(K2/(t \cdot K3))}$$

wherein
$P_0$=1 bar
$T_1$=100° C.
T=temperature inside the reactor, in ° C.

K2=constant equal to 7745 K·nm
t=temperature inside the reactor as K
K3=average diameter of the catalyst pores; and c. at the end of the start up, maintaining the $P_{H2O}/P_{H2}$ and $P_{H2O}/Z$ ratios substantially the same as, or lower than 0.8, by operating on the same operative parameters of the two phases previously described.

* * * * *